United States Patent [19]
Luft

[11] Patent Number: 5,120,511
[45] Date of Patent: Jun. 9, 1992

[54] ADSORBER BED LIFE MONITOR

[75] Inventor: Paul J. Luft, Covington, Va.

[73] Assignee: Westvaco Corporation, New York, N.Y.

[21] Appl. No.: 593,055

[22] Filed: Oct. 5, 1990

[51] Int. Cl.$^5$ .............................................. G01J 1/50
[52] U.S. Cl. ...................................... 422/86; 422/56; 422/57; 422/58; 422/88; 436/121; 436/124
[58] Field of Search .................. 422/56, 86, 58, 57, 422/88; 436/121, 124

[56] References Cited

U.S. PATENT DOCUMENTS

| | | | |
|---|---|---|---|
| 2,234,499 | 3/1941 | McAllister | 422/86 |
| 2,489,654 | 11/1949 | Main-Smith et al. | 422/86 |
| 2,606,102 | 8/1952 | Cook | 422/56 |
| 3,847,552 | 11/1974 | Hobgood et al. | 422/56 |
| 4,115,067 | 9/1978 | Lynshkow | 422/56 |
| 4,205,043 | 5/1980 | Esch et al. | 422/56 |
| 4,256,694 | 3/1981 | McAllister et al. | 422/58 |
| 4,271,121 | 6/1981 | Diller et al. | 422/56 |
| 4,279,773 | 7/1981 | Franey et al. | 252/408 |
| 4,328,181 | 5/1982 | Anders et al. | 422/56 |
| 4,472,353 | 9/1984 | Moore | 422/58 |
| 4,485,665 | 12/1984 | Norman | 422/56 |
| 4,795,611 | 1/1989 | van der Smissen | 422/56 |

Primary Examiner—James C. Housel
Assistant Examiner—Maureen M. Wallenhorst
Attorney, Agent, or Firm—W. A. Marcontell; R. L. Schmalz

[57] ABSTRACT

Chlorine and hydrogen sulfide contamination in a local atmosphere is removed by drafting a ventilation flow stream of the contaminated atmosphere over an activated carbon adsorber bed. Saturation of the adsorber bed by adsorbed contaminant occurs as a progressive front advancing along the flow stream direction. One or more chlorine and hydrogen sulfide sensitive monitors signal passage of the saturation front at designated bed depth points. Each monitor is exposed to a small air sample flow from the bed at the respectively designated point. Each sample flow is directed serially over two reactive paper filters: the first being impregnated with 0-toluidine to remove $Cl_2$ and the second being impregnated with lead acetate to remove $H_2S$. Both filters respond to the respective compounds with a color change. Monitor construction and assembly places both filters side-by-side behind transparent chamber windows for manual observation of the color change without disassembly of the monitor unit.

6 Claims, 3 Drawing Sheets

ADSORBER BED LIFE MONITOR

BACKGROUND OF THE INVENTION

1. Field of the Invention

The present invention relates to adsorbent processes of air purification. More particularly, the invention is directed to a monitor apparatus for signaling the relative state of adsorber bed saturation.

2. Description of the Prior Art

Atmospheres surrounding chemical processing facilities are frequently contaminated with small quantities of chlorine and hydrogen sulfide. Although of low concentration, such contaminants are extremely destructive of certain instrumentation and data processing control equipment.

Responsively, vulnerable instruments and data processing equipment are placed in environmentally controlled enclosures which are ventilated by purified air.

To remove the destructive compounds from the localized atmosphere, a ventilation flow stream drawn from the contaminated ambient air is forced through a bed of particulate activated carbon which adsorptively retains the contaminant compounds.

In time and usage, a given adsorber bed will saturate its adsorption capacity for a particular compound and must be either replaced or regenerated. Operating experience with adsorber bed technology has revealed that such saturation progresses through the bed as a wave band traveling parallel with the air flow stream direction. Air flow within the adsorber bed passing through the saturation band is completely free of contaminant compound. Air flow behind the moving band front is contaminated by degree of proximity to the front. As the actively adsorbing band advances through the adsorber bed, adsorbent behind the band is saturated and therefore no longer contributes toward contaminant removal from the flow stream.

To track progress of the actively adsorbing band for the purpose of predicting the approximate time of total bed saturation, the prior art has used several indicator or monitor techniques. One such technique has been a copper, silver or gold plated monitor rod inserted up the bed depth. $Cl_2$ and $H_2S$ corrode the metal within and behind the actively adsorbing band front. Positional advancement of a visually discerned line of discoloration is correlated to time differentials to predict complete saturation of the adsorber bed. Record keeping necessitates removal of the monitor rod from the adsorber bed to measure the location of the line of color discontinuity. Such discoloration is assumed to represent corrosion. However, the degree or rate of discoloration is highly influenced by the relative humidity of the air flow stream. Consequently, corrosion on copper cannot be gauged solely by discoloration.

Another prior art bed monitoring technique relies upon the measurement of electrical characteristic changes within a metallic tag imbedded within the adsorbent bed. As the metal tag corrodes responsively to $Cl_2$ or $H_2S$ exposure, electrical resistance across the corroded tag increases. This evaluation technique is also highly responsive to relative humidity.

A third prior art bed monitoring technique engages the use of color responsive permeable membranes across sample air flow streams drawn from predetermined bed positions. These permeable membranes are usually filter papers impregnated with reactive compounds selected for chromatic change properties responsive to a second compound exposure, i.e. $H_2S$ and $Cl_2$. In some cases, X-ray fluorescent techniques are required to evaluate the membranes. These impregnated filters are arranged in a stacked series that requires disassembly of the monitor unit to evaluate the report.

An objective of the present invention, therefore, is to provide a chromatic bed monitor unit that requires no disassembly for contamination appraisal.

Another object of the present invention is to provide an adsorber bed monitor that presents all impregnated membranes in a single, continuously visible plane.

Another object of the present invention is to provide a series flow sequence of chromatically responsive, permeable membranes wherein a first membrane in the sequence removes compounds that give misleading chromatic responses from a subsequent membrane in the sequence.

SUMMARY OF THE INVENTION

These and other objects of the invention to be subsequently explained are provided by a laminated assembly of two labrynith blocks between outside face covering plates. Sample flow stream passages within the labrynith blocks guide an air sampling flow stream through a series of chromatically responsive permeable membranes arranged in the same face plane between the two labrynith block inner faces whereby all membranes may be visually evaluated continuously through a transparent cover plate.

BRIEF DESCRIPTION OF THE DRAWINGS

Relative to the drawings wherein like reference characters designate like or similar elements throughout the several figures of the drawings.

DESCRIPTION OF THE PREFERRED EMBODIMENT

Figure 1:
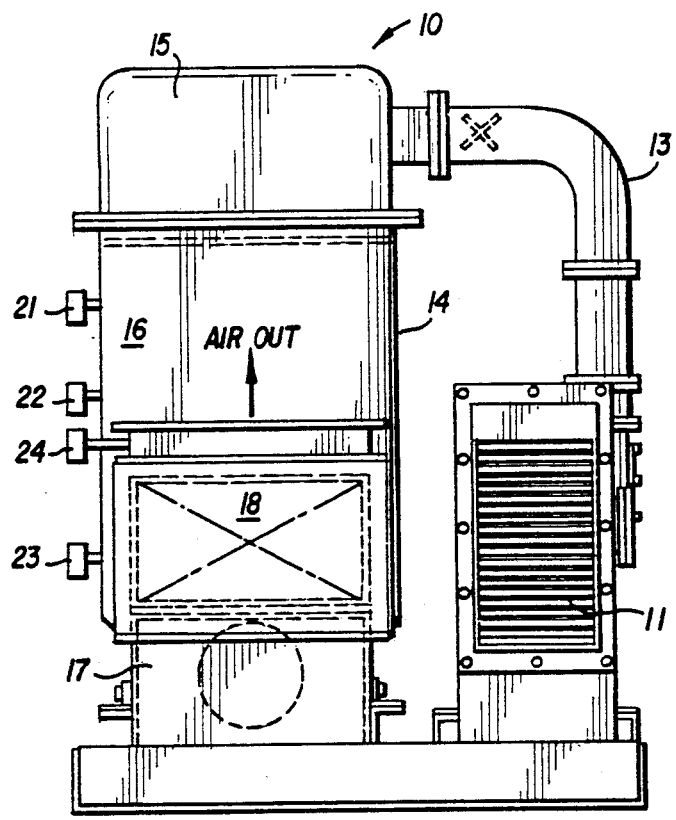
FIG. 1 is a front elevation of a vapor adsorber unit.
Figure 2:
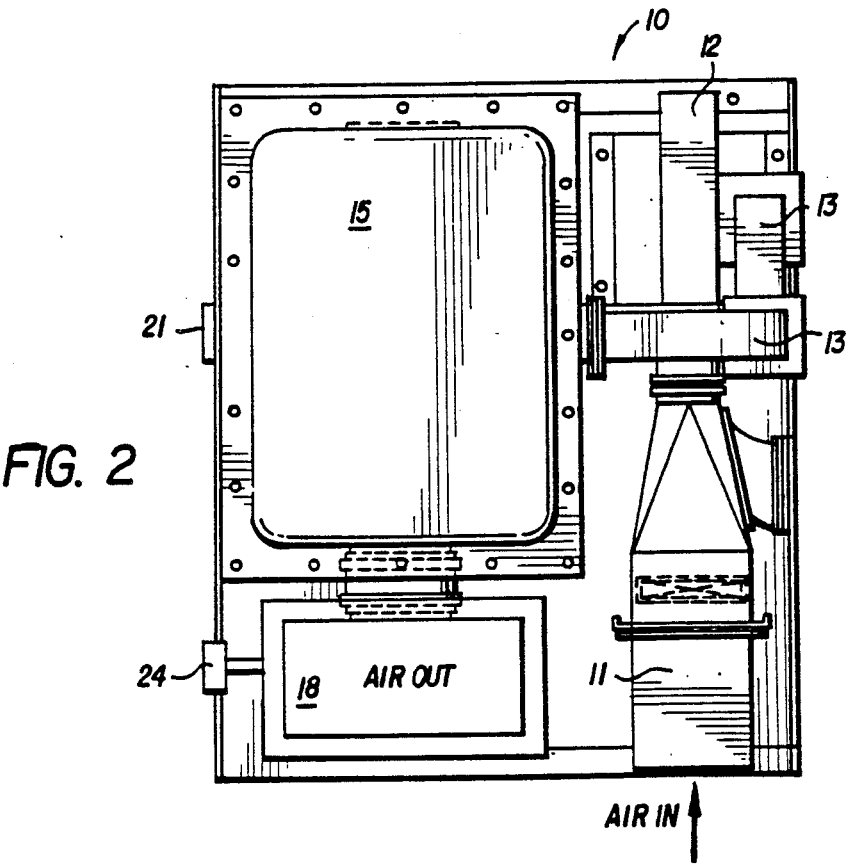
FIG. 2 is a top plan of a vapor adsorber unit.
Figure 3:
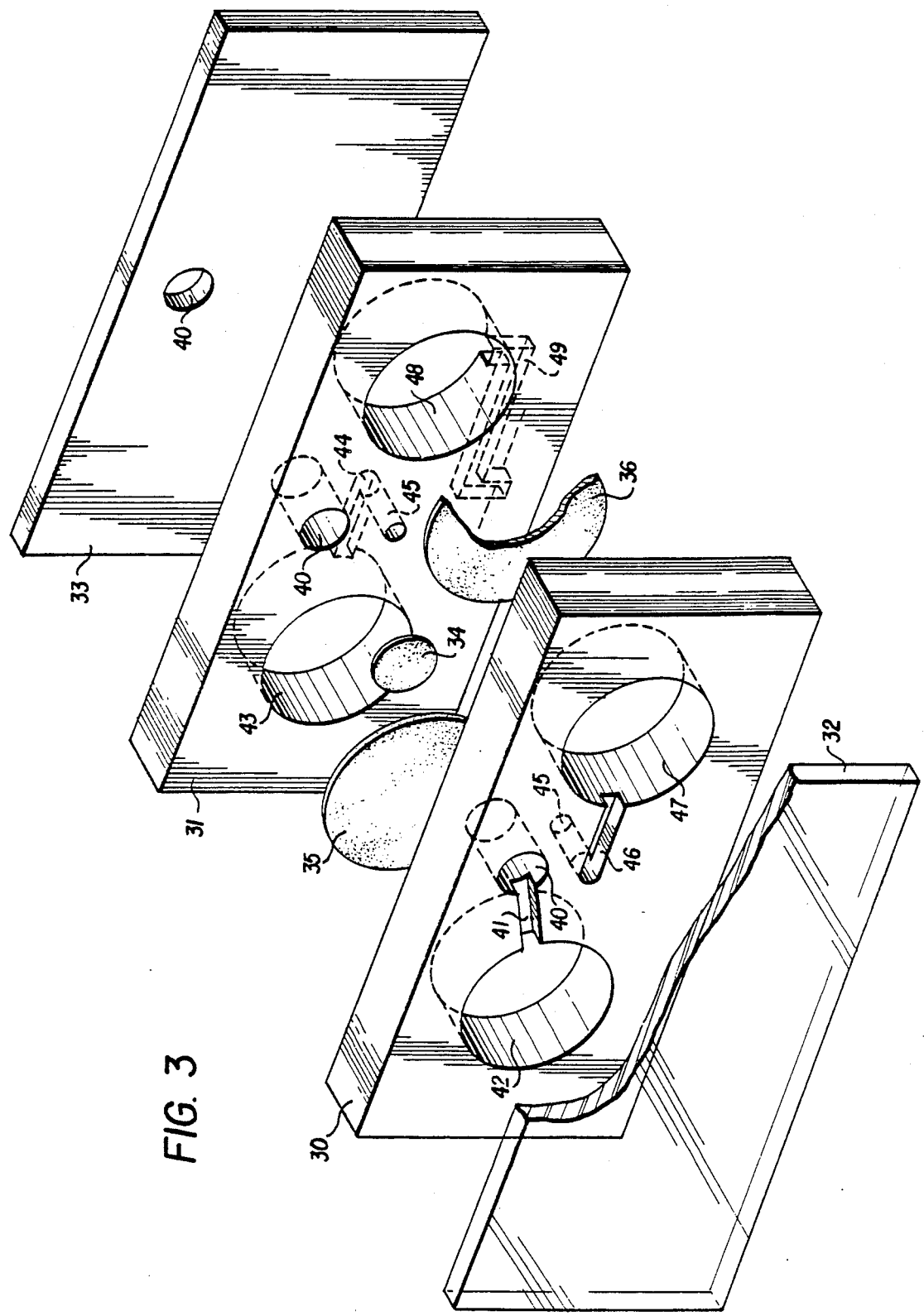
FIG. 3 is an exploded isometric view of the presently disclosed monitor.
Figure 4:
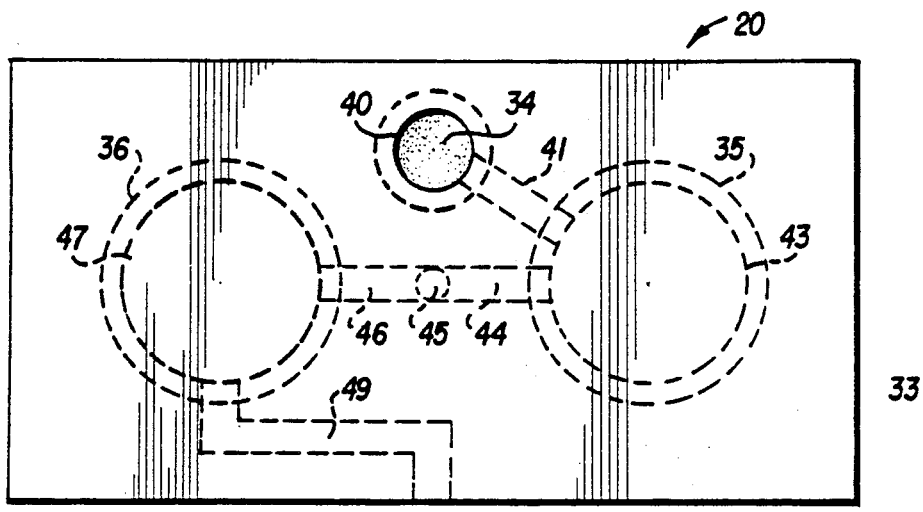
FIG. 4 is a front elevational view of the presently disclosed monitor.
Figure 5:
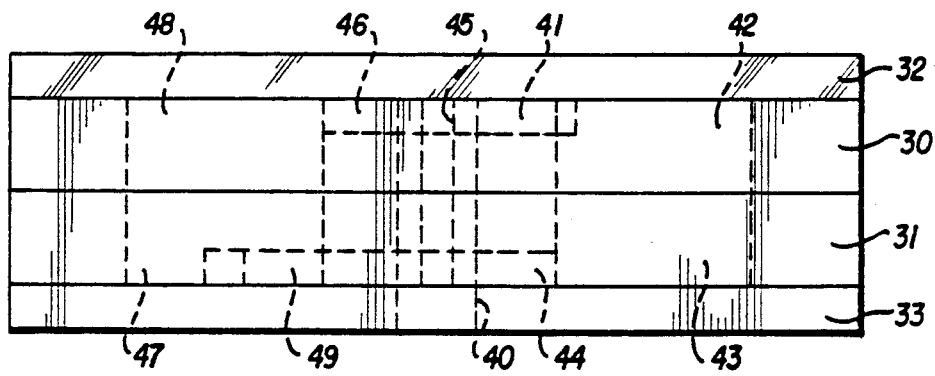
FIG. 5 is a top plan of the presently disclosed monitor.
Figure 6:
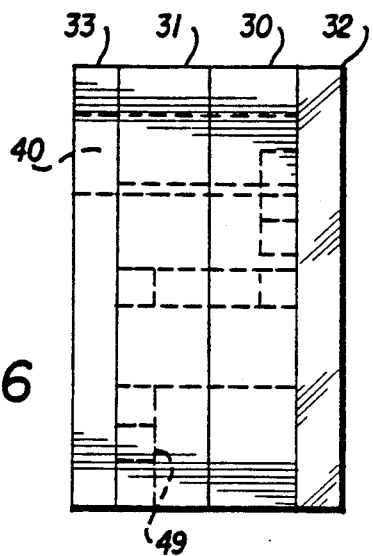
FIG. 6 is an end elevation of the presently disclosed monitor.

Adsorbent process air purification plants may take numerous forms and configurations. That illustrated by FIGS. 1 and 2 as a unitized apparatus 10 is merely representative and includes an enclosed ducting system with an ambient air intake 11. A motor driven fan 12 powers a draft of air flow into the intake 11 and transfer ducting 13 for delivery to an adsorber tank 14.

Air from the transfer ducting 13 enters a distribution plenum 15 for downflow transit through an adsorbent medium bed; usually of specially treated activated carbon particles. An exit plenum 17 receives the purified air flowing from the bottom or discharge end of the adsorbent bed and channels the flow toward a discharge vent 18. Usually, the discharge vent is connected to facility distribution ducting not shown such as an air conditioning system. Equipment to be protected by the purified air flow is housed within a protective enclosure, also not shown, served by the distribution ducting. A low positive air pressure from the purification unit 10 is maintained within the protective enclosure to preclude a reverse leakage flow of contaminated air into the protective enclosure.

Depending on the degree of ambient air contamination and the air flow rate through the purification unit 10, the medium bed will saturate with removed, i.e. adsorbed, contaminants within a finite time period. Such saturation does not arrive uniformly throughout the medium bed, however. Beginning at the top or inlet face of the medium bed, contaminants are adsorbed by a thickness band of medium. Air flow passing through the band is contaminant free and therefore does not contribute to an adsorbed load on medium below the band.

As medium within the adsorbently active band approaches saturation limits, the lower face of the band or front advances into the bed reserve. This process continues until the entire bed is traversed by the active band and there is no more reserve. At this point, the entire bed is spent of its adsorptive capacity and must be replaced or regenerated.

The only manifestation of a saturated absorbent medium bed is the presence of airborne contaminants in the discharge air flow therefrom. Frequently, such discharge flow contamination is of such low concentration as to be imperceptible to human senses. Nevertheless, the contamination is high enough to quickly damage sensitive electronic equipment, the prevention of which is the primary vapor adsorber objective. Consequently, the event of adsorbent bed saturation is frequently unacceptable.

One rational approach toward the prevention of adsorbent bed saturation is to monitor the rate at which the active adsorbent band progresses through the bed for the purpose of anticipating the approximate date of saturation. For this purpose, monitor units 21, 22, 23 and 24 are installed against the adsorber tank wall on respective sample air flow conduits. Air pressure within the adsorber tank forces a small sample air flow through each monitor. Passage of the adsorbently active band past a respective conduit connection point is signified by a color change in the monitor filter capons 35 and 36. Notation of the date on which each monitor begins a color change provides the essential data necessary to predict the date of total bed saturation: assuming a substantially constant level of atmospheric contamination and hence, adsorbent bed usage rate.

Monitor 21 is located on the tank 14 at a point one-sixth along the bed depth. Monitor 22 senses the one-half bed depth position whereas monitor 23 senses the five-sixths bed depth position. Monitor 24 detects the presence of $Cl_2$ and $H_2S$ at the air discharge vent 18.

Relative to FIGS. 3 through 6, monitor construction anticipates a laminated assembly of two labyrinth blocks 30 and 31 between face plates 32 and 33. Preferably, all four block and plate units are of transparent material. However, such characteristic is essential only for the front face plate 32.

Labyrinth blocks 30 and 31 are each formed with four axially aligned through bores. Bore 40 in both blocks is the sample flow inlet channel which also includes an aligned bore opening through back cover plate 33. A Whatman No. 42 paper particulate filter 34 separates the respective block chambers of bore 40. This opening may be threaded to receive a pipe nipple or other conduit connection to and through the adsorber tank 14 wall.

From the bore opening 40 in block 30, a channel 41 directs sample air flow into the chamber of bore 42 which is aligned with bore 43 in labyrinth block 31. These bore chambers are separated by an O-toluidine impregnated Whatman No. 42 paper filter 35.

Air sample flow from the bore chamber 43 follows channel 44 into bore 45 which is axially aligned with bore 45 in labyrinth block 30. Channel 46 connects the bore 45 with the chamber of bore 47.

Bore chamber 47 in block 30 is axially aligned with bore chamber 48 in block 31 but the two are separated by a lead acetate impregnated Whatman No. 42 paper filter 36.

Exit channel 49 carries the sample air flow from the bore chamber 48 into the ambient atmosphere.

The foregoing monitor construction places both color responsive contaminant filters 35 and 36 side-by-side in the same plane for simultaneous viewing through the transparent window of front cover plate 32 without monitor unit disassembly. Cover plates 32 and 33 may be permanently bonded to respective faces of labyrinth blocks 30 and 31. However the face joint between block 30 and 31 must remain separable for the replacement of filters 34, 35 and 36. Any removable clamp bolt, screw or other compression fastener not shown may be used to compress the contiguous faces of labyrinth blocks 30 and 31 against each other and the filters therebetween.

It is significant to note the order of impregnated filters 35 and 36 in the sample air flow route. O-toluidine of filter 35 responds to $Cl_2$ by a color change to dark blue. However, O-toluidine has no visible response to $H_2S$. The lead acetate impregnant of filter 36 has a viable reaction response to $H_2S$ by turning dark brown or black. However, lead acetate also visibly reacts to bleaching effects of $Cl_2$. Consequently, it is essential that the $Cl_2$ reactive filter precede the $H_2S$ filter in the sample flow stream to remove all $Cl_2$ from the sample flow prior to the $H_2S$ filter.

A three week field test of the aforedescribed monitor found a filter 35 impregnated with a 2.5% weight solution of O-toluidine dissolved in acetone to be visually responsive to a 0.1 ppb $Cl_2$ concentration in a 0.9 to 1.6 liter per minute sample flow stream. Similarly, the lead acetate impregnated filter responded chromatically to a 0.3 ppb concentration of $H_2S$ over the same time and sample flow rate range.

Although the invention has been described relative to only two chromatically responsive filters 35 and 36, those of ordinary skill in the art will readily perceive that the labyrinth pattern in blocks 30 and 31 may be expanded to include three or more bore sets 42/43 and 47/48.

Having fully described my invention,

I claim:

1. An article for detecting the presence of selected contaminant compounds in a gas sample flow stream channeled through said article, said article comprising first and second labyrinth blocks, each such block having inside and outside parallel face planes and a plurality of chambers between said face planes, said chambers being positioned within said labyrinth blocks for paired alignment when said respective inside face planes are positioned contiguously wherein first, second, third and final chambers in said first block respectively align with first, second, third and final chambers in said second block, further comprising channels in said blocks located in said outside face planes connecting said second block first chamber with said second block second chamber, connecting said first block second chamber with said first block third chamber, connecting said second block third chamber with said second block final chamber, and connecting said final chamber in said first block with ambient atmosphere, first and second plates covering said first and second block outside face planes for sealing said chambers and channels from ambient atmosphere, said first plate being penetrated by an inlet flow conduit for directing a gas sample flow stream into said first block first chamber, at least one of said plates being substantially transparent, gas permeable membranes separating a plurality of said aligned pairs of chambers at the interface between said contiguously positioned inside face planes, respective chromatically responsive reagent means impregnating said permeable membranes between at least two of said aligned pairs of chambers for reacting with respective color changes to the presence of respectively predetermined contaminants in said gas sample flow stream and clamping means holding said blocks, plates and membranes in contiguous laminated assembly.

2. An article as described by claim 1 wherein one of said gas permeable membranes is a particular filter means which separates said first aligned chamber pair.

3. An article as described by claim 2 wherein said membranes separating respective aligned chambers of said second and final aligned chamber pairs are impregnated with said respective chromatically responsive reagent means.

4. An article as described by claim 3 wherein said second chamber membrane reagent means is reactive to only one contaminant compound in said gas sample flow stream.

5. An article as described by claim 4 wherein said final chamber membrane reagent means is reactive to said one contaminant compound of said second chamber membrane reagent means and at least one other contaminant compound in said gas sample flow stream.

6. An article as described by claim 5 wherein said second chamber membrane reagent means comprises O-toluidine and said final chamber membrane reagent means comprises lead acetate.

* * * * *